(12) United States Patent
Xu et al.

(10) Patent No.: US 9,291,564 B2
(45) Date of Patent: Mar. 22, 2016

(54) METHOD AND APPARATUS FOR ALIGNING MEASURED SPECTRAL RADIANCE FACTORS AMONG DIFFERENT INSTRUMENTS

(71) Applicant: Datacolor Holding AG, Lucerne (CH)

(72) Inventors: Zhiling Xu, West Windsor, NJ (US); Michael H. Brill, Kingston, NJ (US)

(73) Assignee: Datacolor Holding AG, Lucerne (CH)

( * ) Notice: Subject to any disclaimer, the term of this patent is extended or adjusted under 35 U.S.C. 154(b) by 399 days.

(21) Appl. No.: 13/857,564

(22) Filed: Apr. 5, 2013

(65) Prior Publication Data
US 2014/0299787 A1 Oct. 9, 2014

(51) Int. Cl.
G01N 21/64 (2006.01)
G01N 21/27 (2006.01)

(52) U.S. Cl.
CPC ............ *G01N 21/645* (2013.01); *G01N 21/276* (2013.01)

(58) Field of Classification Search
CPC ..................................................... G01N 21/64
USPC .......... 250/459.1, 458.1, 461.1, 484.2, 486.1, 250/252.1, 363.09
See application file for complete search history.

(56) References Cited

U.S. PATENT DOCUMENTS

| | | | | |
|---|---|---|---|---|
| 5,107,445 A * | 4/1992 | Jensen | ............... | G01K 11/3213 374/161 |
| 5,384,641 A | 1/1995 | Imura | | |
| 5,636,015 A * | 6/1997 | Imura | .................. | G01J 3/4406 250/461.1 |
| 6,020,959 A * | 2/2000 | Imura | ....................... | G01J 3/02 250/461.1 |
| 6,264,107 B1 * | 7/2001 | Thomas, III | ............. | G06K 7/12 235/462.02 |
| 6,535,278 B1 | 3/2003 | Imura | | |
| 6,607,300 B1 * | 8/2003 | Kleinerman | ........... | G01K 11/20 250/483.1 |
| 6,791,688 B2 * | 9/2004 | Lai | ..................... | G01N 21/6402 250/458.1 |
| 6,996,252 B2 * | 2/2006 | Reed | ..................... | G06T 1/0042 235/491 |
| 7,002,162 B1 * | 2/2006 | Fujimoto | ........... | G01N 21/6445 250/458.1 |
| 7,067,824 B2 * | 6/2006 | Muller | ................... | G06K 19/14 250/458.1 |
| 7,213,757 B2 * | 5/2007 | Jones | ..................... | B41M 3/144 235/380 |
| 7,262,420 B1 * | 8/2007 | MacLeod | ............... | G07D 7/122 250/458.1 |
| 7,595,473 B2 * | 9/2009 | Walt | ......................... | G01J 3/02 250/205 |
| 7,675,620 B2 * | 3/2010 | Imura | .................. | G01N 21/251 356/300 |

(Continued)

OTHER PUBLICATIONS

Lee et al. ,Spectral Estimation and Color Appearance Prediction of Fluorescent Material, Proceedings of SPIE vol. 4080, 2000.*

(Continued)

*Primary Examiner* — David Porta
*Assistant Examiner* — Djura Malevic

(57) ABSTRACT

Aligning measurements of fluorescent spectral radiance factors taken by a first instrument with measurements of fluorescent spectral radiance factors taken by a second instrument, without knowledge of the matrix of bispectral luminescent radiance factor of any sample, includes obtaining a fluorescent spectral radiance factor of a reference sample, measured by the first instrument, obtaining the fluorescent spectral radiance factor of the reference sample, measured by the second instrument, obtaining a fluorescent spectral radiance factor of a test sample, measured by the first instrument, and estimating the fluorescent spectral radiance factor of the test sample that would be measured by the second instrument, based on the fluorescent spectral radiance factor of a reference sample, measured by the first instrument, on the fluorescent spectral radiance factor of the reference sample, measured by the second instrument, and on the fluorescent spectral radiance factor of the test sample, measured by the first instrument.

20 Claims, 9 Drawing Sheets

(56) References Cited

U.S. PATENT DOCUMENTS

| | | | | |
|---|---|---|---|---|
| 7,750,802 | B1* | 7/2010 | Parish | G01N 21/64 250/370.01 |
| 8,288,739 | B2* | 10/2012 | Imura | G01N 21/645 250/458.1 |
| 9,029,800 | B2* | 5/2015 | Kiesel | G01J 3/36 250/458.1 |
| 2002/0020818 | A1* | 2/2002 | Mitchell | G01N 21/6408 250/459.1 |
| 2002/0131618 | A1* | 9/2002 | Ahlers | G07D 7/122 382/101 |
| 2002/0158212 | A1* | 10/2002 | French | B01L 3/50853 250/459.1 |
| 2003/0058441 | A1* | 3/2003 | Shakespeare | G01J 3/28 356/319 |
| 2006/0020403 | A1* | 1/2006 | Pusiol | G01F 1/716 702/45 |
| 2007/0189595 | A1* | 8/2007 | Giering | G07D 7/122 382/137 |
| 2008/0137086 | A1* | 6/2008 | Imura | G01N 21/251 356/433 |
| 2008/0149855 | A1* | 6/2008 | Mehta | G01N 21/5911 250/492.1 |
| 2008/0186494 | A1* | 8/2008 | Kiesel | G01N 21/0303 356/440 |
| 2008/0230715 | A1* | 9/2008 | Nielsen | A61B 5/05 250/458.1 |
| 2009/0086892 | A1* | 4/2009 | Boyden | A61B 5/415 378/44 |
| 2009/0086894 | A1* | 4/2009 | Boyden | A61B 6/00 378/44 |
| 2009/0086900 | A1* | 4/2009 | Boyden | G01N 23/223 378/45 |
| 2009/0086901 | A1* | 4/2009 | Boyden | A61B 5/415 378/45 |
| 2009/0086902 | A1* | 4/2009 | Boyden | A61B 5/415 378/45 |
| 2009/0108214 | A1* | 4/2009 | Shinoda | G01N 15/1425 250/492.1 |
| 2009/0194705 | A1* | 8/2009 | Kiesel | G01N 21/645 250/458.1 |
| 2009/0266999 | A1* | 10/2009 | Krattiger | A61B 1/00096 250/459.1 |
| 2010/0108910 | A1* | 5/2010 | Morrell | G01N 15/0205 250/459.1 |
| 2010/0155577 | A1* | 6/2010 | Kiesel | G01N 15/1056 250/208.2 |
| 2010/0201988 | A1* | 8/2010 | Kiesel | G01N 21/05 356/419 |
| 2011/0052082 | A1* | 3/2011 | Parkov | G06K 9/2018 382/209 |
| 2011/0090485 | A1* | 4/2011 | Cronin | G07D 7/122 356/71 |
| 2011/0241549 | A1* | 10/2011 | Wootton | F21S 8/006 315/117 |

OTHER PUBLICATIONS

NPL, Fifth Oxford Conference on Spectrometry 2006, Holopainen et al.).*
JP translations of 2012-134868.*
Lin et al. ,Factors affecting the whiteness of optically brightened material, J. Opt. Soc. Am A vol. 29, No. 11 Nov. 2012).*
M. Brill, "Minimal Von Kries Illuminant Invariance" Jun. 2007. Revised Sep. 14, 2007, accepted Sep. 18, 2007. pp. 320-323.
K. Imura, "New Method for Measuring an Optical Property of a Sample Treated by FWA" Jul. 11, 2006, revised Aug. 28, 1996 accepted Sep. 1, 2006. vol. 32 No. 3, Jun. 2007. pp. 195-200.
Brum et al. "Optical Radiation Measurements" vol. 2, 1980. Chapter 6, Section X: "Instrumentation in Fluorescence Measurements" pp. 246-248.

* cited by examiner

METHOD AND APPARATUS FOR ALIGNING MEASURED SPECTRAL RADIANCE FACTORS AMONG DIFFERENT INSTRUMENTS

FIELD OF THE INVENTION

The present invention generally relates to the measurement of spectral radiance, and more specifically relates to the coordination of multiple instruments that measure spectral radiance.

BACKGROUND

Optical brightening agents (OBAs) are additives used to enhance the appearance of color of fabric and paper. In particular, OBAs cause a "whitening" effect that makes materials look less yellow by increasing the overall amount of blue light reflected.

Sometimes, "whiteness" represented as a single number is not sufficient for the study of OBA-enhanced paper or fabric samples. Instead, a total spectral radiance factor (TSRF) is used to express more detailed information about a sample. TSRF is defined as the ratio of spectral radiance illuminated and observed under the same conditions at wavelength λ of an observed fluorescent sample and of a completely diffuse, non-fluorescent, perfectly reflecting surface. Alternatively, TSRF may be defined as the ratio of the flux intensity at wavelength λ returned from the fluorescent sample and from the completely diffuse reflecting surface in the same solid angle of the same direction, when illuminated under the same conditions. Thus, TSRF may be expressed as:

$$B(\lambda)=S(\lambda)/S_0(\lambda) \quad \text{(EQN. 1)}$$

where $S(\lambda)$ is the intensity at wavelength λ of the radiant light returned by the fluorescent sample, and $S_0(\lambda)$ is the intensity at wavelength λ of the radiant light reflected by the completely diffuse reflecting surface.

In general, $B(\lambda)$ includes two parts, as expressed below:

$$B(\lambda)=R(\lambda)+\phi(\lambda) \quad \text{(EQN. 2)}$$

where $R(\lambda)$ is the reflection spectral radiance factor (i.e., reflectance) and $\phi(\lambda)$ is the fluorescent spectral radiance factor.

Although $R(\lambda)$ is purely sample related, $\phi(\lambda)$ is the ratio of fluorescent light and diffuse reflection of the illuminant light and depends on the light source as well as on the sample. For different instruments, the spectral power distribution of the light source can be dramatically different; thus, the directly measured TSRF of the same sample by different instruments can vary dramatically. Conventional approaches that compensate for instrument differences are algorithmically complicated and require prior knowledge of certain measurements.

SUMMARY OF THE INVENTION

In one embodiment, aligning measurements of fluorescent spectral radiance factors taken by a first instrument with measurements of fluorescent spectral radiance factors taken by a second instrument includes obtaining a fluorescent spectral radiance factor of a reference fluorescent sample, as measured by the first instrument, obtaining the fluorescent spectral radiance factor of the reference fluorescent sample, as measured by the second instrument, obtaining a fluorescent spectral radiance factor of a test fluorescent sample, as measured by the first instrument, and estimating the fluorescent spectral radiance factor of the test fluorescent sample that would be measured by the second instrument, based on the fluorescent spectral radiance factor of a reference fluorescent sample, as measured by the first instrument, on the fluorescent spectral radiance factor of the reference fluorescent sample, as measured by the second instrument, and on the fluorescent spectral radiance factor of the test fluorescent sample, as measured by the first instrument, wherein the method is performed without knowledge of a matrix of a bispectral luminescent radiance factor of any sample.

In another embodiment, aligning measurements of fluorescent spectral radiance factors taken by a first instrument with measurements of fluorescent spectral radiance factors taken by a second instrument includes obtaining a first measurement, the first measurement comprising a total spectral radiance factor of a reference fluorescent sample as measured by the first instrument in an ultraviolet-included configuration, obtaining a second measurement, the second measurement comprising the total spectral radiance factor of the reference fluorescent sample as measured by the second instrument in an ultraviolet-included configuration, obtaining a third measurement, the third measurement comprising a reflectance of the reference fluorescent sample as measured by the first instrument in an ultraviolet-excluded configuration, obtaining a fourth measurement, the fourth measurement comprising the reflectance of the reference fluorescent sample as measured by the second instrument in an ultraviolet-excluded configuration, obtaining a fifth measurement, the fifth measurement comprising a total spectral radiance factor of a test fluorescent sample as measured by the first instrument in the ultraviolet-included configuration, obtaining a sixth measurement, the sixth measurement comprising a reflectance of the test fluorescent sample as measured by the first instrument in the ultraviolet-excluded configuration, and estimating a fluorescent spectral radiance factor of the test fluorescent sample that would be measured by the second instrument, in accordance with the first measurement, the second measurement, the third measurement, the fourth measurement, the fifth measurement, and the sixth measurement, wherein the method is performed without knowledge of a matrix of a bispectral luminescent radiance factor of any sample.

In another embodiment, aligning measurements of fluorescent spectral radiance factors taken by a first instrument with measurements of fluorescent spectral radiance factors taken by a second instrument includes obtaining a first measurement, the first measurement comprising a ratio of a sample channel raw signal to a reference channel raw signal for a white color standard as measured by the second instrument calibrated in an ultraviolet-included configuration, obtaining a second measurement, the second measurement comprising a ratio of a sample channel raw signal to a reference channel raw signal for a reference fluorescent sample as measured by the second instrument calibrated in the ultraviolet-included configuration, obtaining a third measurement, the third measurement comprising the ratio of the sample channel raw signal to the reference channel raw signal for the reference fluorescent sample as measured by the second instrument operating in an ultraviolet-excluded configuration, calculating a fluorescent spectral radiance factor of the reference fluorescent sample as measured by the second instrument, in accordance with the first measurement, the second measurement, and the third measurement, obtaining a fourth measurement, the fourth measurement comprising the ratio of the sample channel raw signal to the reference channel raw signal for the white color standard as measured by the first instrument calibrated in an ultraviolet-included configuration, obtaining a fifth measurement, the fifth measurement comprising the ratio of the sample channel raw signal to the reference channel raw signal for the reference fluorescent sample as measured by the first instrument calibrated in the ultraviolet-included configuration, obtaining a sixth measurement, the sixth measurement comprising the ratio of the sample channel raw signal to the reference channel raw signal for the reference fluorescent sample as measured by the first instrument operating in an ultraviolet-excluded configuration, calculating the fluorescent spectral radiance factor of the reference fluorescent sample as measured by the first instrument, in accordance with the fourth measurement, the fifth measurement, and the sixth measurement, and calculating an adjustment factor that aligns the measurements of fluorescent spectral radiance factors taken by the first instrument with the measurements of the fluorescent spectral radiance factors taken by the second instrument, in accordance with the fluorescent spectral radiance factor of the reference fluorescent sample as measured by the second instrument and the fluorescent spectral radiance factor of the reference fluorescent sample as measured by the first instrument.

BRIEF DESCRIPTION OF THE DRAWINGS

The teachings of the present invention can be readily understood by considering the following detailed description in conjunction with the accompanying drawings, in which.

DETAILED DESCRIPTION

In one embodiment, the present invention includes a method and apparatus for aligning measured spectral radiance factors among different instruments. The instruments are measurement instruments that measure the optical properties of samples containing fluorescent material. Embodiments of the invention calibrate a test instrument using a known reference instrument and a reference fluorescent sample. A test fluorescent sample is then measured using the calibrated test instrument, and the resultant measurement emulates a measurement of the test fluorescent sample by the reference instrument. Thus, the measurement of the test fluorescent sample by the test instrument may be considered a "virtual" measurement of the test fluorescent sample by the reference instrument. The disclosed methods do not require knowledge of any sample's matrix of bispectral luminescent radiance factor.

As discussed above, when measuring total spectral radiance factor (TSRF) using different instruments, the fluorescent spectral radiance factor part $\phi(\lambda)$ is dependent on the illumination source. Without any adjustment, the measurement result can be dramatically different from instrument to instrument.

Figure 1:
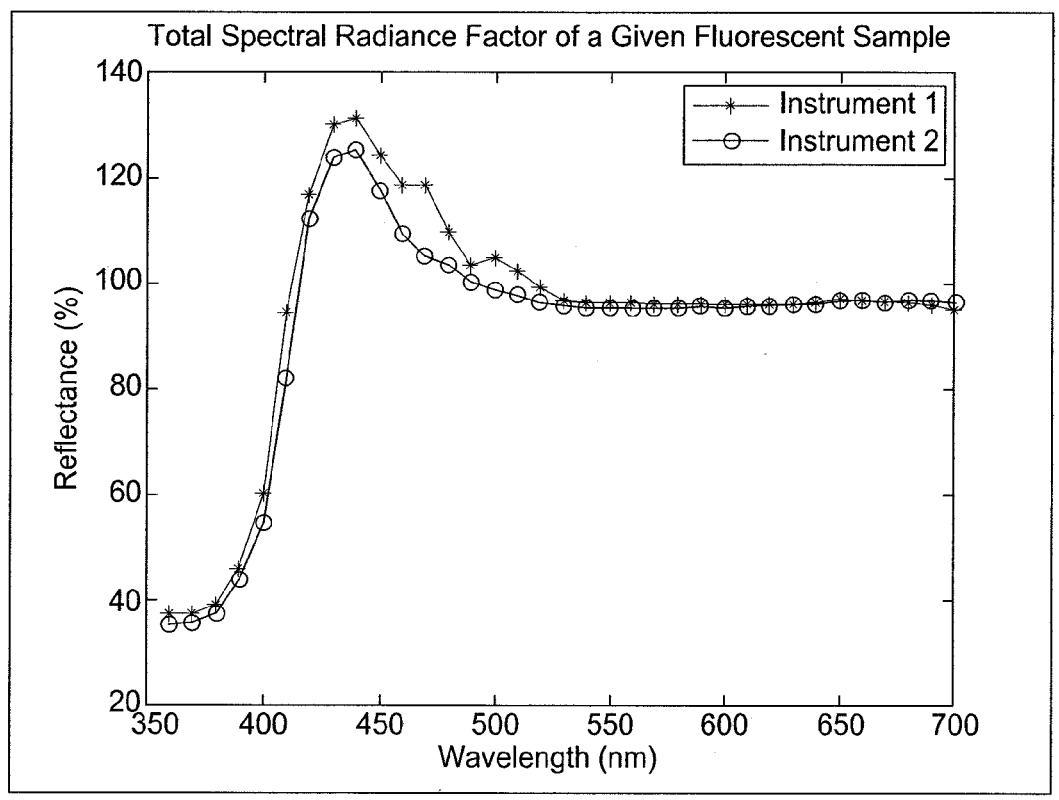
FIG. 1 is a line graph illustrating the total spectral radiance factor for a single sample as measured by two different instruments.
Figure 2:
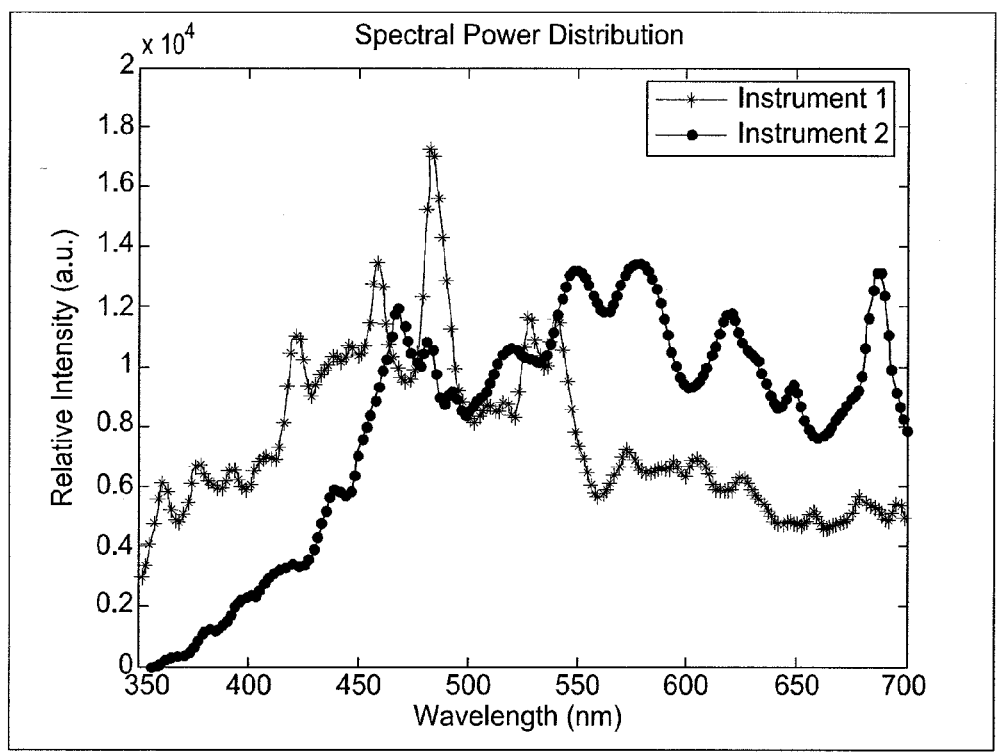
FIG. 2 is a line graph illustrating the spectral power distributions of the respective light sources that are part of the two different instruments referenced in FIG. 1.

FIG. 1, for example, is a line graph illustrating the total spectral radiance factor for a single sample as measured by two different instruments (identified in FIG. 1 as "Instrument 1" and "Instrument 2"). FIG. 2 is a line graph illustrating the spectral distributions of the respective light sources that are part of the two different instruments referenced in FIG. 1. Referring simultaneously to FIGS. 1 and 2, it is clear that since the light sources of the two different instruments have different spectral power distributions, the measured TSRF peaks between approximately 420 nanometers and approximately 550 nanometers have different shapes. However, if a user has been using Instrument 2 and believes that the measurements made by Instrument 2 have been correct, he may, on viewing FIG. 2, now believe that the measurements made by Instrument 2 are wrong. Embodiments of the invention can be used to align Instrument 2 with Instrument 1, so that the measurements made by Instrument 2 are similar to measurements made by Instrument 1.

The fluorescent spectral radiance factor $\phi(\lambda)$ of EQN. 2 (above) can be written as:

$$\phi(\lambda)=\int F(\mu,\lambda)I(\mu)d\mu/I(\lambda) \quad \text{(EQN. 3)}$$

where $F(\mu, \lambda)$ is the bispectral luminescent radiance factor (input-to-output matrix) that characterizes the fluorescent material.

If one assumes that:

$$F(\mu,\lambda)=e(\mu)f(\lambda) \quad \text{(EQN. 4)}$$

then the fluorescent emission depends on the light source only through the intensity of its excitation of the fluorescent material; the shape of the fluorescent spectrum from the fluorescent material remains unchanged when the illuminant is changed.

Designating Illuminant 1 and Illuminant 2 as $I_1(\lambda)$ and $I_2(\lambda)$, respectively, and designating x and y as two samples, one can derive:

$$\Phi_{1x}(\lambda) = \int e_x(\mu)I_1(\mu)d\mu \frac{f_x(\lambda)}{I_1(\lambda)} \quad \text{(EQN. 5)}$$

$$\Phi_{1y}(\lambda) = \int e_y(\mu)I_1(\mu)d\mu \frac{f_y(\lambda)}{I_1(\lambda)} \quad \text{(EQN. 6)}$$

$$\Phi_{2x}(\lambda) = \int e_x(\mu)I_2(\mu)d\mu \frac{f_x(\lambda)}{I_2(\lambda)} \quad \text{(EQN. 7)}$$

$$\Phi_{2y}(\lambda) = \int e_y(\mu) I_2(\mu) d\mu \frac{f_y(\lambda)}{I_2(\lambda)} \qquad \text{(EQN. 8)}$$

One can further assume that:

$$\frac{\int e_x(\mu) I_1(\mu) d\mu}{\int e_x(\mu) I_2(\mu) d\mu} = \frac{\int e_y(\mu) I_1(\mu) d\mu}{\int e_y(\mu) I_2(\mu) d\mu} \qquad \text{(EQN. 9)}$$

Spectral conditions underlying the assumption of EQN. 9 are discussed in further detail in the Appendix. Adopting this assumption, one develops the following:

$$\frac{\Phi_{1x}(\lambda)}{\Phi_{2x}(\lambda)} = \frac{\Phi_{1y}(\lambda)}{\Phi_{2y}(\lambda)} \qquad \text{(EQN. 10)}$$

Or, equivalently, $$\Phi_{2x}(\lambda) = \Phi_{1x}(\lambda) \frac{\Phi_{2y}(\lambda)}{\Phi_{1y}(\lambda)} \qquad \text{(EQN. 11)}$$

EQN. 11 states that if one knows the fluorescent spectral radiance factor ϕ of a reference fluorescent sample y under two different illuminants (i.e., Illuminant 1 and Illuminant 2), and if one also knows the fluorescent spectral radiance of a test fluorescent sample x under one of those illuminants (e.g., Illuminant 1), one can calculate the fluorescent spectral radiance of the test fluorescent sample x under the other illuminant (i.e., Illuminant 2). Specific methods for exploiting this fact in order to align one instrument with another (i.e., so that their measured TSRFs look similar) are discussed in further detail with respect to FIGS. 3 and 4, below.

Figure 3:
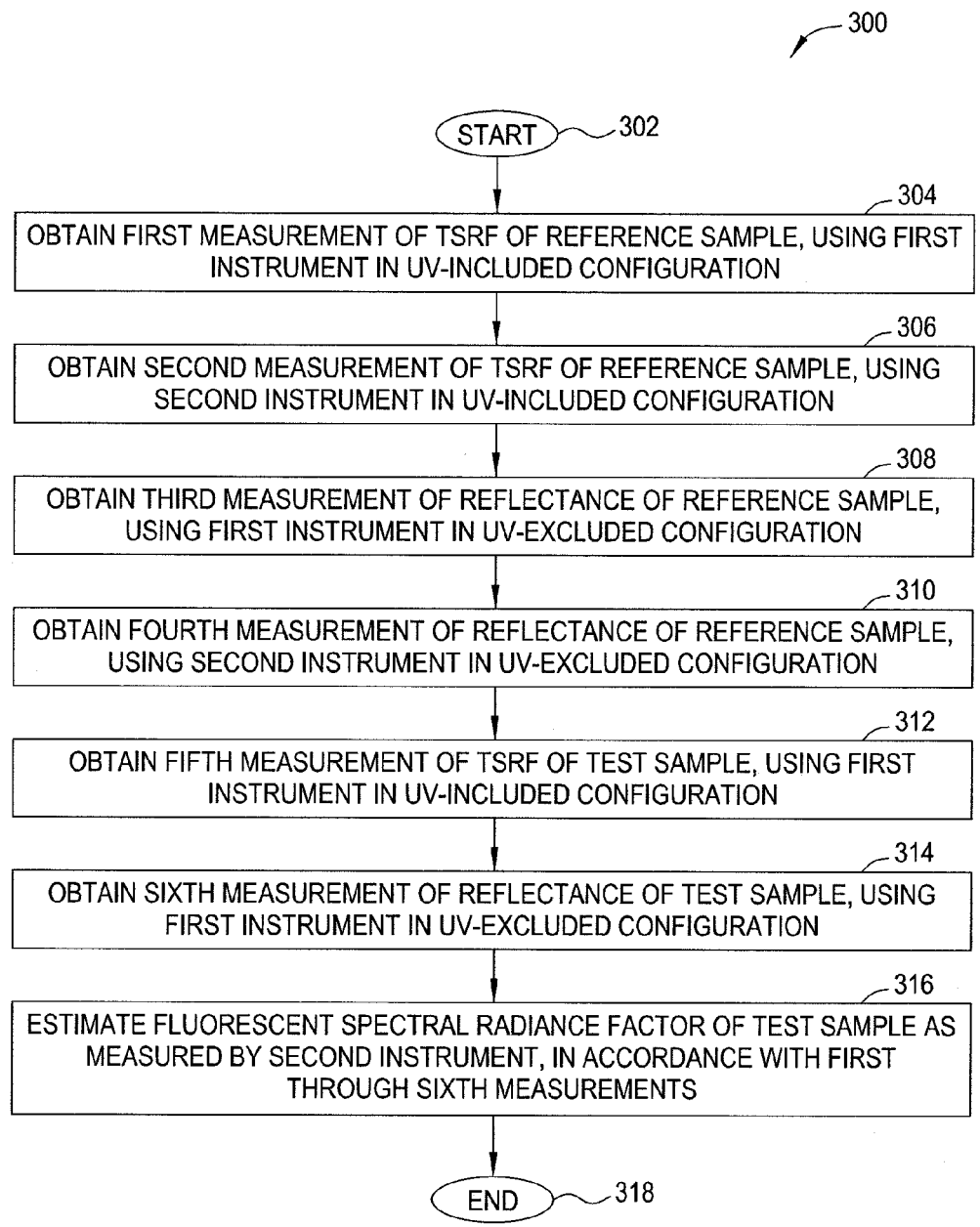
FIG. 3 is a flow diagram illustrating one embodiment of a method for aligning the measured total spectral radiance factors of two different measurement instruments, according to the present invention.

FIG. 3 is a flow diagram illustrating one embodiment of a method 300 for aligning the measured total spectral radiance factors of two different measurement instruments, according to the present invention. The method 300 may be performed, for example, by a processor that is configured to receive measurements made by the two instruments.

The method 300 assumes the existence of a first instrument (i.e., a test instrument, referred to as "Instrument 1"), a second instrument (i.e., a reference instrument, referred to as "Instrument 2"), a test sample including fluorescent material (referred to as "sample x"), and a reference sample including fluorescent material (referred to as "sample y"). The method 300 further assumes that Instrument 1 and Instrument 2 both include an ultraviolet (UV) cutoff filter that allows the instrument to be configured in UV-included mode (i.e., without the UV cutoff filter blocking the optical path) or UV-excluded mode (i.e., with the UV cutoff filter blocking the optical path). Furthermore, the method 300 assumes that Instrument 1 and Instrument 2 have both been pre-calibrated (e.g., using a while color standard) in both the UV-included configuration and the UV-excluded configuration.

To calculate the fluorescent spectral radiance of the test fluorescent sample x under Illuminant 2 (i.e., $\phi_{2x}(\lambda)$), one needs to know the three fluorescent spectral radiance quantities $\phi_{1x}$, $\phi_{2y}$, and $\phi_{1y}$ on the right-hand side of EQN. 11. For a given instrument and sample, one first measures quantities B (total spectral radiance factor when the UV-blocking filter is out of the optical path of the given instrument) and R (reflectance, which is the total spectral radiance factor when the UV-blocking filter is in the optical path). Using the relation of EQN. 2 yields:

$$\phi_{1x}(\lambda) = B_{1x}(\lambda) - R_{1x}(\lambda)$$

$$\phi_{1y}(\lambda) = B_{1y}(\lambda) - R_{1y}(\lambda)$$

$$\phi_{2y}(\lambda) = B_{2y}(\lambda) - R_{2y}(\lambda) \qquad \text{(EQN. 12)}$$

Thus, EQN. 11 becomes:

$$\Phi_{2x}(\lambda) = [B_{1x}(\lambda) - R_{1x}(\lambda)] \frac{B_{2y}(\lambda) - R_{2y}(\lambda)}{B_{1y}(\lambda) - R_{1y}(\lambda)} \qquad \text{(EQN. 13)}$$

Accordingly, the method 300 begins in step 302. In step 304, a first measurement is obtained. The first measurement is a measurement of the total spectral radiance factor $B_{1y}$ of the reference fluorescent sample y, using the first instrument (Instrument 1) in the UV-included configuration.

In step 306, a second measurement is obtained. The second measurement is a measurement of the total spectral radiance factor $B_{2y}$ of the reference fluorescent sample y, using the second instrument (Instrument 2) in the UV-included configuration.

In step 308, a third measurement is obtained. The third measurement is a measurement of the reflectance $R_{1y}$ of the reference fluorescent sample y, using the first instrument (Instrument 1) in the UV-excluded configuration.

In step 310, a fourth measurement is obtained. The fourth measurement is a measurement of the reflectance $R_{2y}$ of the reference fluorescent sample y, using the second instrument (Instrument 2) in the UV-excluded configuration.

Steps 304-310 thus provide all of the data needed to align the measurements of Instrument 1 and Instrument 2 (e.g., according to EQN. 13). That is, having made the first, second, third, and fourth measurements using the reference sample, one can now measure any test sample x using Instrument 1 and then estimate what Instrument 2 would measure for the test sample x, as discussed in further detail with respect to steps 312-316.

In step 312, a fifth measurement is obtained. The fifth measurement is a measurement of the total spectral radiance factor $B_{1x}$ of the test fluorescent sample x, using the first instrument (Instrument 1) in the UV-included configuration.

In step 314, a sixth measurement is obtained. The sixth measurement is a measurement of the reflectance $R_{1x}$ of the test fluorescent sample x, using the first instrument (Instrument 1) in the UV-excluded configuration.

In step 316, the fluorescent spectral radiance factor $\phi_{2x}(\lambda)$ of the test fluorescent sample x as measured by the second instrument (Instrument 2) is estimated in accordance with the first, second, third, fourth, fifth, and sixth measurements (e.g., using EQN. 13).

The method 300 ends in step 318.

In summary, the ratio $$\frac{B_{2y}(\lambda) - R_{2y}(\lambda)}{B_{1y}(\lambda) - R_{1y}(\lambda)}$$

in EQN. 13 is an adjustment factor between a "test" instrument (e.g., Instrument 1) and a "reference" instrument (e.g., Instrument 2). Once this adjustment factor is calculated using a reference sample (e.g., reference sample y), one can use the test instrument to measure any test sample (e.g., test sample x) and to estimate the fluorescent spectral radiance factor of the test sample that would be directly measured by the reference instrument.

Figure 4:
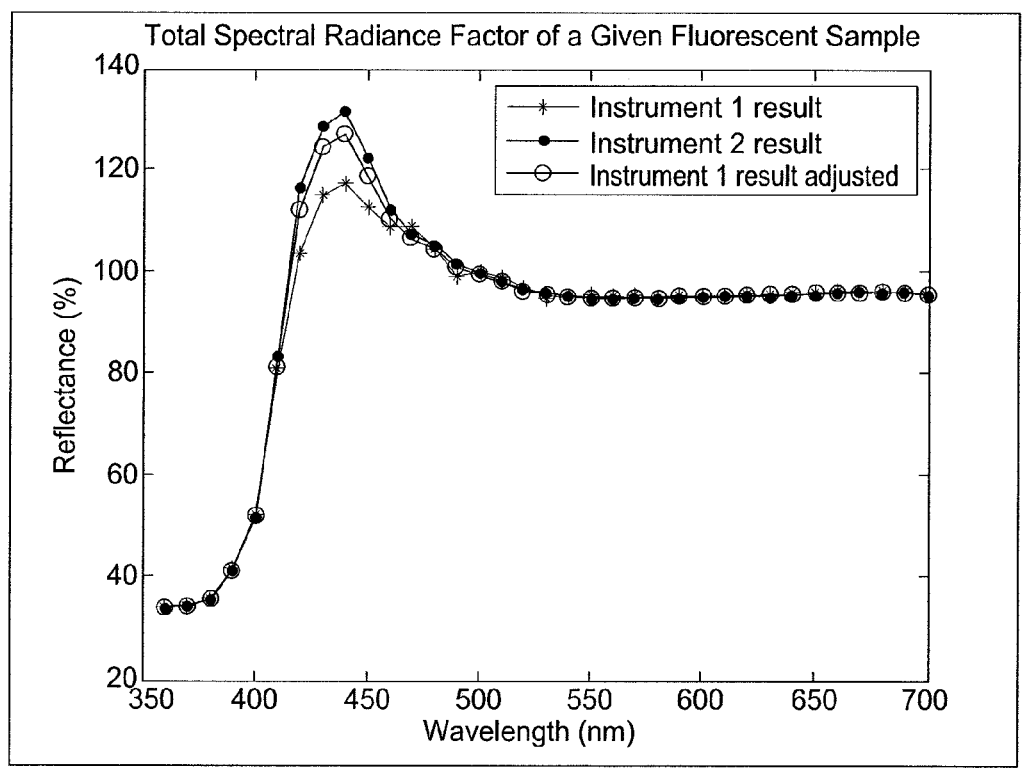
FIG. 4 is a line chart illustrating the total spectral radiance factor measurement results for a fluorescent sample made using a test instrument before and after being adjusted to a reference instrument, using the method illustrated in FIG. 3.

FIG. 4 is a line chart illustrating the TSRF measurement results for a first fluorescent sample made using a test instrument (identified as "Instrument 1") before and after being adjusted to a reference instrument (identified as "Instrument 2"), using the method 300 illustrated in FIG. 3. As FIG. 4 illustrates, the measurement result using the test instrument after the adjustment is more aligned to the measurement result using the reference instrument.

Figure 5:
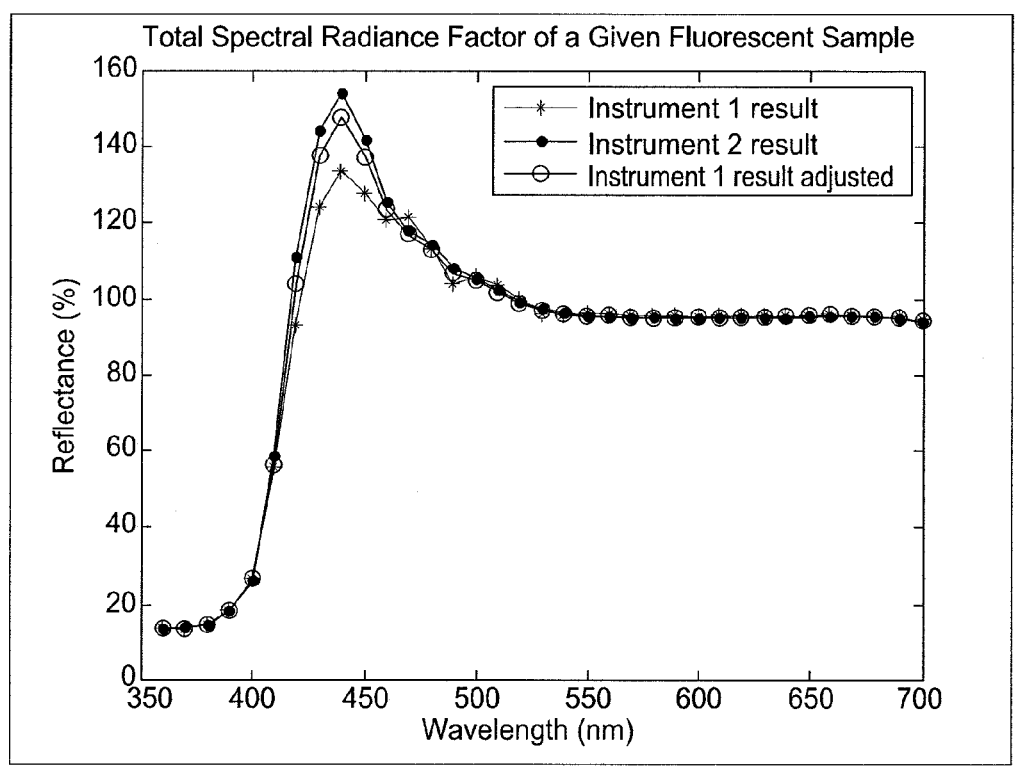
FIG. 5 is a line chart illustrating the total spectral radiance factor measurement result for a second fluorescent sample (i.e., a different fluorescent sample from the first fluorescent sample referenced in FIG. 4) using a test instrument before and after being adjusted to a reference instrument, using the first fluorescent sample referenced in FIG. 4 as a reference sample and using the method illustrated in FIG. 3 to perform the adjustment.

FIG. 5 is a line chart illustrating the TSRF measurement result for a second fluorescent sample (i.e., a different fluorescent sample from the first fluorescent sample referenced in FIG. 4) using a test instrument (identified as "Instrument 1") before and after being adjusted to a reference instrument (identified as "Instrument 2"), using the first fluorescent sample referenced in FIG. 4 as a reference sample and using the method 300 to perform the adjustment. As FIG. 5 illustrates, the measurement result using the test instrument is more aligned to the measurement result using the reference instrument.

As discussed above, the method 300 assumes that Instrument 1 and Instrument 2 have both been pre-calibrated (e.g., using a while color standard) in both the UV-included configuration and the UV-excluded configuration. Reflectance data is then measured directly. However, in an alternative embodiment, Instrument 1 and Instrument 2 may be pre-calibrated only in the UV-included configuration. In this case, sample channel and a reference channel raw data may be used to calculate fluorescent spectral radiance factors.

If SOR is defined as the ratio of the sample channel raw signal to the reference channel raw signal, then EQN. 2 may be rewritten as:

$$\Phi(\lambda) = \frac{SOR_{UVIn}(\lambda)}{SOR_{whiteUVIn}(\lambda)} R_{white}(\lambda) - \frac{SOR_{UVEx}(\lambda)}{SOR_{whiteUVEx}(\lambda)} R_{white}(\lambda) \quad \text{(EQN. 14)}$$

where $R(\lambda)$ is the reflectance data of the calibration white color standard, $SOR_{whiteUVIn}(\lambda)$ is the SOR of the white calibration color standard measured without the UV cutoff filter (i.e., during UV-included calibration), $SOR_{whiteUVEx}(\lambda)$ is the SOR of the white calibration color standard measured with the UV cutoff filter (i.e., during UV-excluded calibration), $SOR_{UVIn}(\lambda)$ is the SOR of the fluorescent sample measured without the UV cutoff filter, and $SOR_{UVEx}(\lambda)$ is the SOR of the fluorescent sample measured with the UV cutoff filter.

Considering that $SOR_{whiteUVIn}(\lambda) = SOR_{whiteUVEx}(\lambda)$, EQN. 14 can be rewritten as:

$$\Phi(\lambda) = \frac{SOR_{UVIn}(\lambda) - SOR_{UVEx}(\lambda)}{SOR_{whiteUVIn}(\lambda)} R_{white}(\lambda) \quad \text{(EQN. 15)}$$

one only needs to do the UV-included calibration once in order to collect the white color standard raw data.

Figure 6:
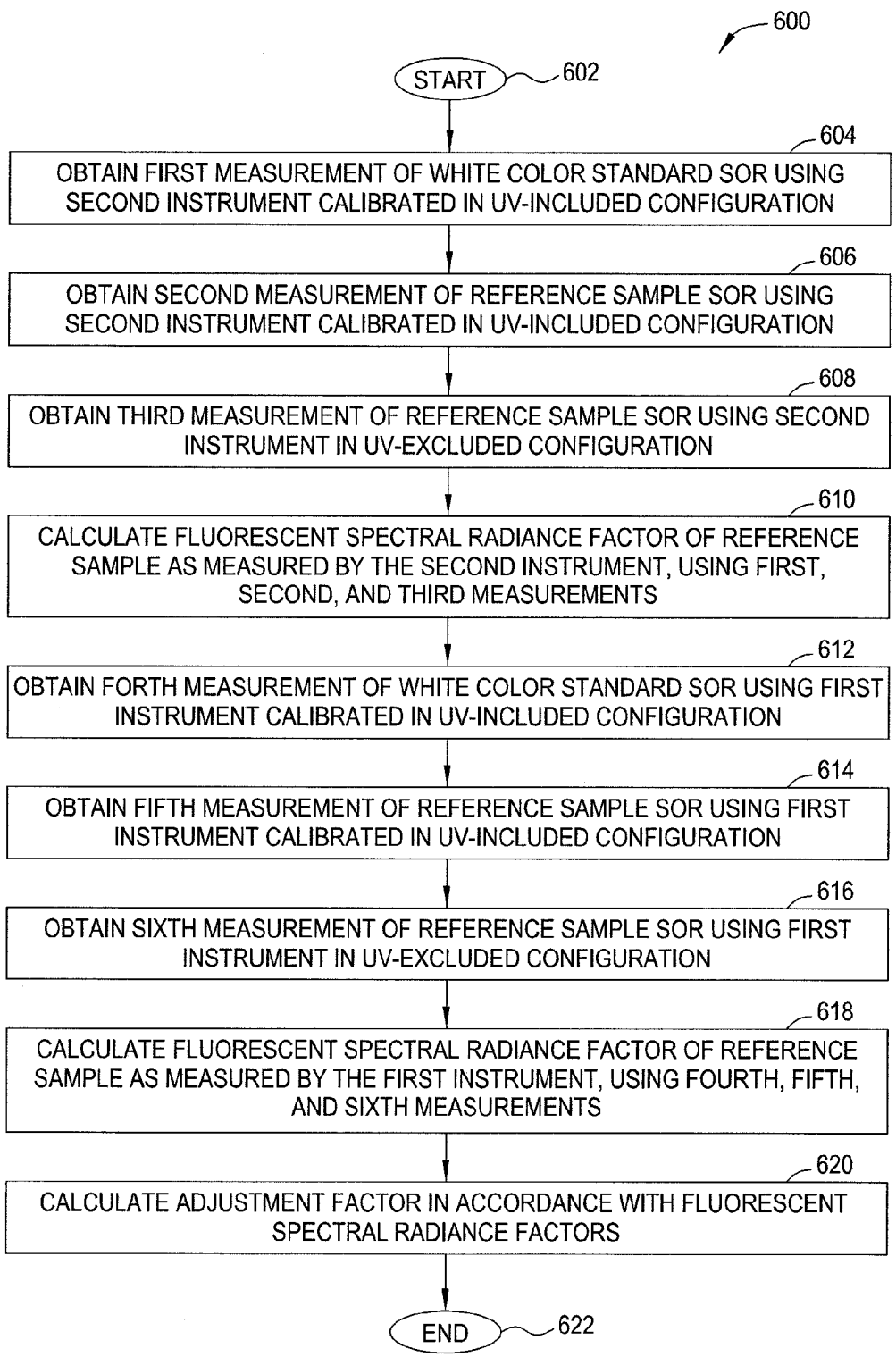
FIG. 6 is a flow diagram illustrating one embodiment of a method for aligning the measured total spectral radiance factors of two different measurement instruments, according to the present invention.

FIG. 6 is a flow diagram illustrating one embodiment of a method 600 for aligning the measured total spectral radiance factors of two different measurement instruments, according to the present invention. The method 600 may be performed, for example, by a processor that is configured to receive measurements made by the two instruments.

Like the method 300, the method 600 assumes the existence of a first instrument (i.e., a test instrument, referred to as "Instrument 1"), a second instrument (i.e., a reference instrument, referred to as "Instrument 2"), a test sample including fluorescent material (referred to as "sample x"), and a reference sample including fluorescent material (referred to as "sample y"). The method 600 further assumes that Instrument 1 and Instrument 2 both include an ultraviolet (UV) cutoff filter that allows the instrument to be configured in UV-included mode (i.e., without the UV cutoff filter blocking the optical path) or UV-excluded mode (i.e., with the UV cutoff filter blocking the optical path). Furthermore, the method 600 assumes that Instrument 1 and Instrument 2 have both been pre-calibrated (e.g., using a while color standard) only in the UV-included configuration.

The method 200 begins in step 602. In step 604, a first measurement is obtained. The first measurement is a measurement of the white color standard SOR using the second instrument (Instrument 2) calibrated in the UV-included configuration.

In step 606, a second measurement is obtained. The second measurement is a measurement of the $SOR_{UVIn}$ of a reference fluorescent sample y using the second instrument (Instrument 2) calibrated in the UV-included configuration.

In step 608, a third measurement is obtained. The third measurement is a measurement of the $SOR_{UVEx}$ of the reference fluorescent sample y using the second instrument (Instrument 2) in the UV-excluded configuration (i.e., with the UV cutoff filter blocking the optical path).

In step 610, the fluorescent spectral radiance factor $\phi_{2y}(\lambda)$ of the reference fluorescent sample y as measured by the second instrument (Instrument 2) is calculated using the first, second, and third measurements (e.g., according to EQN. 15).

In step 612, a fourth measurement is obtained. The fourth measurement is a measurement of the white color standard SOR using the first instrument (Instrument 1) calibrated in the UV-included configuration.

In step 614, a fifth measurement is obtained. The fifth measurement is a measurement of the $SOR_{UVIn}$ of a reference fluorescent sample y using the first instrument (Instrument 1) calibrated in the UV-included configuration.

In step 616, a sixth measurement is obtained. The sixth measurement is a measurement of the $SOR_{UVEx}$ of the reference fluorescent sample y using the first instrument (Instrument 1) in the UV-excluded configuration (i.e., with the UV cutoff filter blocking the optical path).

In step 618, the fluorescent spectral radiance factor $\phi_{1y}(\lambda)$ of the reference fluorescent sample y as measured by the first instrument (Instrument 1) is calculated using the fourth, fifth, and sixth measurements (e.g., according to EQN. 15).

In step 620, an adjustment factor is computed. The adjustment factor is the ratio of $\phi_{2y}(\lambda)/\phi_{1y}(\lambda)$ (i.e., the values computed in steps 610 and 618).

The method 600 ends in step 622.

The adjustment factor calculated in step 620 adjusts the first instrument (Instrument 1) to the second instrument (Instrument 2). Thus, once the adjustment factor is calculated, the first instrument (e.g., a "test" instrument) can be used to measure any test sample x by following steps 602-610 to calculate the fluorescent spectral radiance factor $\phi_{1x}(\lambda)$ of the test fluorescent sample x as measured by the first instrument. The fluorescent spectral radiance factor $\phi_{2x}(\lambda)$ of the test fluorescent sample y as would be measured by the second instrument (a "reference" instrument) can then be estimated according to EQN. 11.

Figure 7:
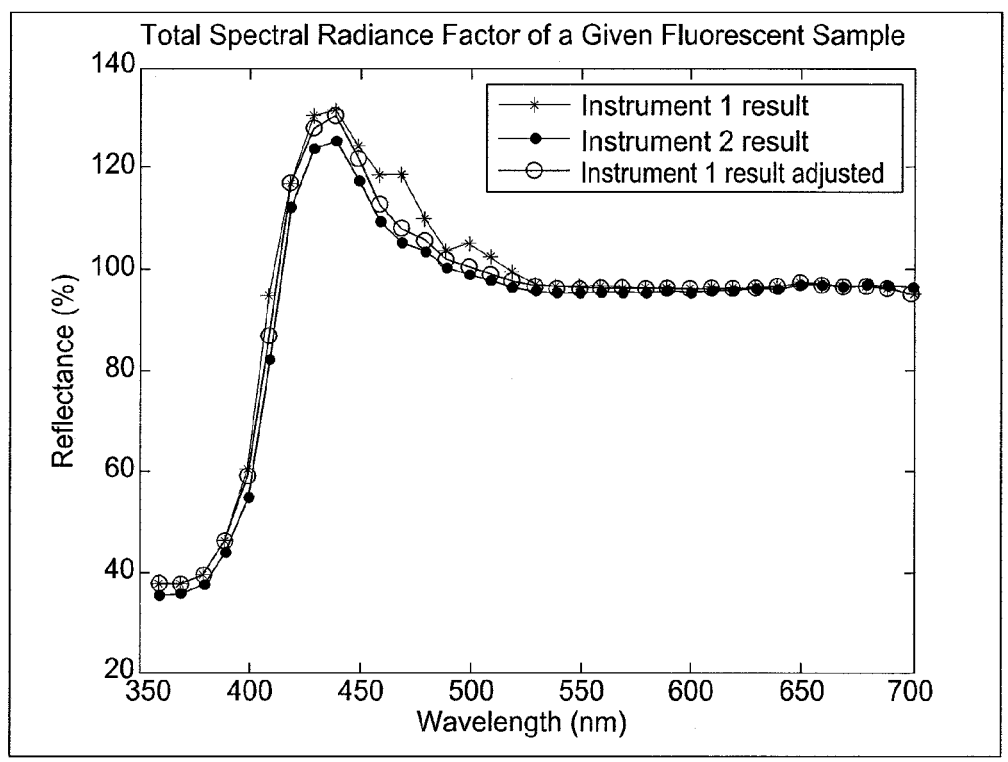
FIG. 7 is a line graph illustrating the total spectral radiance factor measurements of a fluorescent sample taken by a test instrument before and after the test instrument is adjusted to a reference instrument according to the method illustrated in FIG. 6.

FIG. 7 is a line graph illustrating the total spectral radiance factor measurements of a reference fluorescent sample taken by a test instrument (identified as Instrument 1) before and after the test instrument is adjusted to a reference instrument (identified as Instrument 2) according to the method 600 illustrated in FIG. 6. As FIG. 7 illustrates, after the adjustment, the measurements of the reference sample made by the test instrument are more aligned with the measurements of the reference sample made by the reference instrument.

Figure 8:
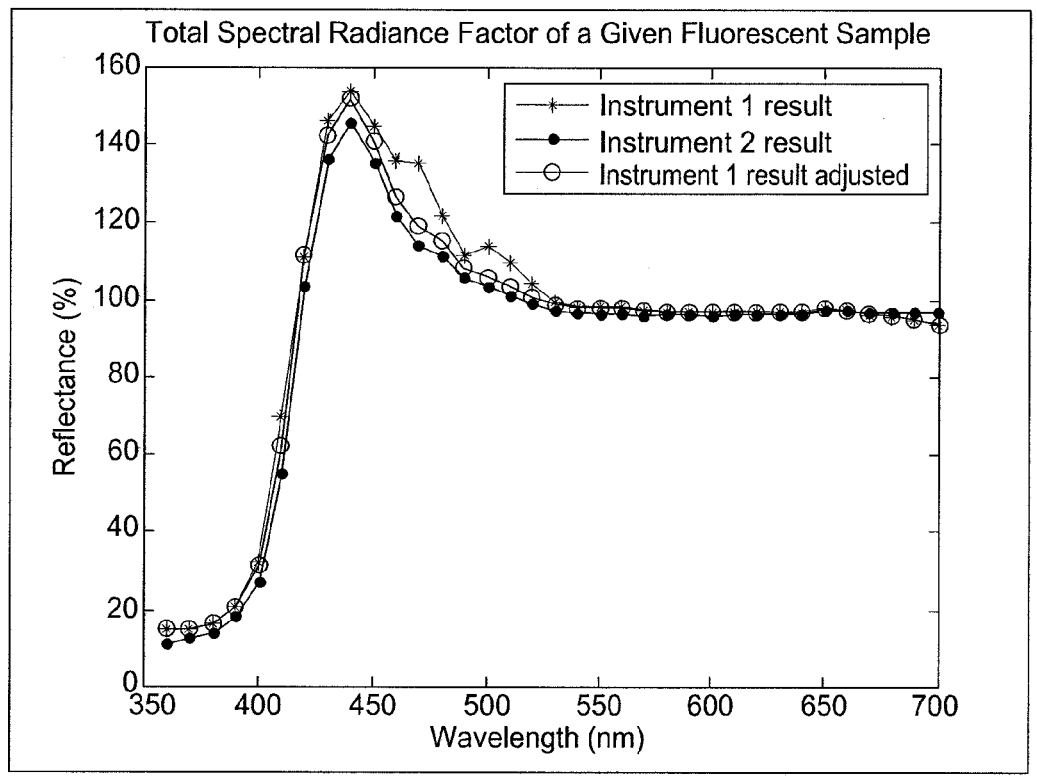
FIG. 8 is a line graph illustrating the total spectral radiance factor measurements of a test fluorescent sample taken by a test instrument before and after the test instrument is adjusted to a reference instrument according to the method 600 illustrated in Figure.

FIG. 8 is a line graph illustrating the total spectral radiance factor measurements of a test fluorescent sample taken by a test instrument (identified as Instrument 1) before and after the test instrument is adjusted to a reference instrument (identified as Instrument 2) according to the method 600 illustrated in FIG. 6. The same reference fluorescent sample used in FIG. 7 is used. As FIG. 8 illustrates, after the adjustment, the measurements of the test sample made by the test instrument are more aligned with the measurements of the test sample made by the reference instrument.

According to embodiments of the disclosed invention, the measurement result of a test fluorescent sample with an instrument that doesn't have a standard illumination can still be adjusted as if the instrument has a standard illumination (e.g., D65), providing that the total spectral radiance factor measurements of a reference sample under standard illumination and under the instrument's non-standard illumination are known.

Figure 9:
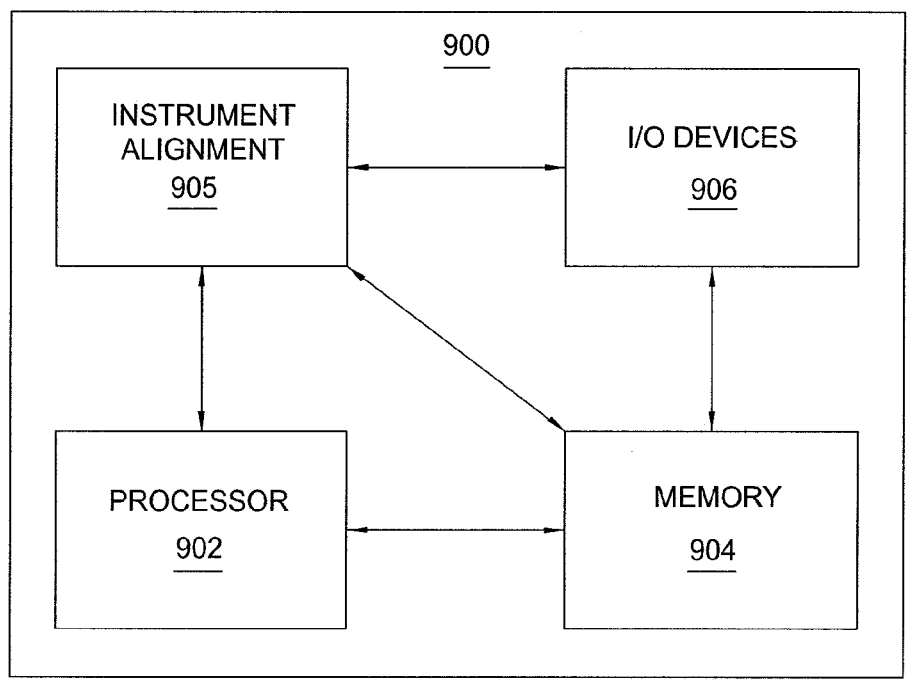
FIG. 9 is a high-level block diagram of the instrument alignment method that is implemented using a general purpose computing device 900.

FIG. 9 is a high-level block diagram of the instrument alignment method that is implemented using a general purpose computing device 900. In one embodiment, a general purpose computing device 900 comprises a processor 902, a memory 904, an instrument alignment module 905 and various input/output (I/O) devices 906 such as a display, a keyboard, a mouse, a stylus, a wireless network access card, an Ethernet interface, and the like. In one embodiment, at least one I/O device is a storage device (e.g., a disk drive, an optical disk drive, a floppy disk drive). It should be understood that the instrument alignment module 905 can be implemented as a physical device or subsystem that is coupled to a processor through a communication channel.

Alternatively, the instrument alignment 905 can be represented by one or more software applications (or even a combination of software and hardware, e.g., using Application Specific Integrated Circuits (ASIC)), where the software is loaded from a storage medium (e.g., I/O devices 906) and operated by the processor 902 in the memory 904 of the general purpose computing device 900. Thus, in one embodiment, the instrument alignment module 905 for aligning the measured total spectral radiance factors of two different measurement instruments, as described herein with reference to the preceding figures, can be stored on a tangible or physical non-transitory computer readable storage medium (e.g., RAM, magnetic or optical drive or diskette, and the like).

It should be noted that although not explicitly specified, one or more steps of the methods described herein may include a storing, displaying and/or outputting step as required for a particular application. In other words, any data, records, fields, and/or intermediate results discussed in the methods can be stored, displayed, and/or outputted to another device as required for a particular application. Furthermore, steps or blocks in the accompanying figures that recite a determining operation or involve a decision, do not necessarily require that both branches of the determining operation be practiced. In other words, one of the branches of the determining operation can be deemed as an optional step.

While the foregoing is directed to embodiments of the present invention, other and further embodiments of the invention may be devised without departing from the basic scope thereof. Various embodiments presented herein, or portions thereof, may be combined to create further embodiments. Furthermore, terms such as top, side, bottom, front, back, and the like are relative or positional terms and are used with respect to the exemplary embodiments illustrated in the figures, and as such these terms may be interchangeable.

APPENDIX A

EQN. 9 of the above disclosure can be rewritten as:

$$<e_x I_1>/<e_x I_2> = <e_y I_1>/<e_y I_2> \quad \text{(EQN. 16)}$$

where $<\ >$ denotes integration over the excitation wavelength $\mu$.

EQN. 16 is true for excitation spectra $e_x$, $e_y$ and for illuminants $I_1$, $I_2$, given that the illuminants $I_1(\mu)$ and $I_2(\mu)$ are orthogonal to the function:

$$g(\mu) = <e_y I_2> e_x(\mu) - <e_x I_2> e_y(\mu) \quad \text{(EQN. 17)}$$

Hence, $$<I_1 g> = <I_2 g> = 0 \quad \text{(EQN. 18)}$$

The sufficiency of this condition is clear from substituting EQN. 17 into EQN. 18. EQN. 18 is a highly constraining condition, but one that can be realized. It is analogous to a condition that must be true for Von Kries chromatic adaptation to give color consistency, which it approximately does.

What is claimed is:

1. A method for aligning measurements of fluorescent spectral radiance factors taken by a first instrument with measurements of fluorescent spectral radiance factors taken by a second instrument, the method comprising:
    obtaining a fluorescent spectral radiance factor of a reference fluorescent sample, as measured by the first instrument;
    obtaining the fluorescent spectral radiance factor of the reference fluorescent sample, as measured by the second instrument;
    obtaining a fluorescent spectral radiance factor of a test fluorescent sample, as measured by the first instrument; and
    estimating the fluorescent spectral radiance factor of the test fluorescent sample that would be measured by the second instrument, based on the fluorescent spectral radiance factor of a reference fluorescent sample, as measured by the first instrument, on the fluorescent spectral radiance factor of the reference fluorescent sample, as measured by the second instrument, and on the fluorescent spectral radiance factor of the test fluorescent sample, as measured by the first instrument,
    wherein the method is performed without knowledge of a matrix of a bispectral luminescent radiance factor of any sample.

2. The method of claim 1, wherein the estimating comprises:
    dividing the fluorescent spectral radiance factor of the reference fluorescent sample, as measured by the second instrument, by the fluorescent spectral radiance factor of a reference fluorescent sample, as measured by the first instrument, to produce a quotient; and
    multiplying the quotient by the fluorescent spectral radiance factor of a test fluorescent sample, as measured by the first instrument, to produce the fluorescent spectral radiance factor of the test fluorescent sample that would be measured by the second instrument.

3. The method of claim 1, wherein the first instrument and the second instrument are both configurable to operate in an ultraviolet-included mode and an ultraviolet-excluded mode.

4. The method of claim 3, wherein the first instrument and the second instrument are both calibrated prior to a perfor-

11 mance of the method, using a white color standard, in both the ultraviolet-included mode and the ultraviolet-excluded mode.

5. The method of claim 4, wherein the obtaining the fluorescent spectral radiance factor of the reference fluorescent sample, as measured by the first instrument, comprises:
measuring a total spectral radiance factor of the reference fluorescent sample using the first instrument in the ultraviolet-included mode, to produce a first measurement;
measuring the total spectral radiance factor of the reference fluorescent sample using the first instrument in the ultraviolet-excluded mode, to produce a second measurement; and
subtracting the second measurement from the first measurement to obtain the fluorescent spectral radiance factor of the reference fluorescent sample.

6. The method of claim 3, wherein the first instrument and the second instrument are both calibrated prior to a performance of the method, using a white color standard, in the ultraviolet-included mode only.

7. The method of claim 6, wherein the obtaining a fluorescent spectral radiance factor of a reference fluorescent sample, as measured by the first instrument, comprises:
obtaining a first measurement, the first measurement comprising a ratio of a sample channel raw signal to a reference channel raw signal for a white color standard as measured by the first instrument calibrated in the ultraviolet-included configuration;
obtaining a second measurement, the second measurement comprising a ratio of a sample channel raw signal to a reference channel raw signal for the reference fluorescent sample as measured by the first instrument calibrated in the ultraviolet-included configuration;
obtaining a third measurement, the third measurement comprising the ratio of the sample channel raw signal to the reference channel raw signal for the reference fluorescent sample as measured by the first instrument operating in the ultraviolet-excluded configuration;
calculating the fluorescent spectral radiance factor of the reference fluorescent sample as measured by the first instrument, in accordance with the first measurement, the second measurement, and the third measurement.

8. A non-transitory computer readable storage medium that stores instructions which, when executed, cause a processor to perform operations comprising:
obtaining a fluorescent spectral radiance factor of a reference fluorescent sample, as measured by the first instrument;
obtaining the fluorescent spectral radiance factor of the reference fluorescent sample, as measured by the second instrument;
obtaining a fluorescent spectral radiance factor of a test fluorescent sample, as measured by the first instrument; and
estimating the fluorescent spectral radiance factor of the test fluorescent sample that would be measured by the second instrument, based on the fluorescent spectral radiance factor of a reference fluorescent sample, as measured by the first instrument, on the fluorescent spectral radiance factor of the reference fluorescent sample, as measured by the second instrument, and on the fluorescent spectral radiance factor of the test fluorescent sample, as measured by the first instrument,
wherein the method is performed without knowledge of a matrix of a bispectral luminescent radiance factor of any sample.

9. The non-transitory computer readable storage medium of claim 8, wherein the estimating comprises:

12 dividing the fluorescent spectral radiance factor of the reference fluorescent sample, as measured by the second instrument, by the fluorescent spectral radiance factor of a reference fluorescent sample, as measured by the first instrument, to produce a quotient; and
multiplying the quotient by the fluorescent spectral radiance factor of a test fluorescent sample, as measured by the first instrument, to produce the fluorescent spectral radiance factor of the test fluorescent sample that would be measured by the second instrument.

10. The non-transitory computer readable storage medium of claim 8, wherein the first instrument and the second instrument are both configurable to operate in an ultraviolet-included mode and an ultraviolet-excluded mode.

11. The non-transitory computer readable storage medium of claim 10, wherein the first instrument and the second instrument are both calibrated prior to a performance of the method, using a white color standard, in both the ultraviolet-included mode and the ultraviolet-excluded mode.

12. The non-transitory computer readable storage medium of claim 11, wherein the obtaining the fluorescent spectral radiance factor of the reference fluorescent sample, as measured by the first instrument, comprises:
measuring a total spectral radiance factor of the reference fluorescent sample using the first instrument in the ultraviolet-included mode, to produce a first measurement;
measuring the total spectral radiance factor of the reference fluorescent sample using the first instrument in the ultraviolet-excluded mode, to produce a second measurement; and
subtracting the second measurement from the first measurement to obtain the fluorescent spectral radiance factor of the reference fluorescent sample.

13. The non-transitory computer readable storage medium of claim 10, wherein the first instrument and the second instrument are both calibrated prior to a performance of the method, using a white color standard, in the ultraviolet-included mode only.

14. The non-transitory computer readable storage medium of claim 13, wherein the obtaining a fluorescent spectral radiance factor of a reference fluorescent sample, as measured by the first instrument, comprises:
obtaining a first measurement, the first measurement comprising a ratio of a sample channel raw signal to a reference channel raw signal for a white color standard as measured by the first instrument calibrated in the ultraviolet-included configuration;
obtaining a second measurement, the second measurement comprising a ratio of a sample channel raw signal to a reference channel raw signal for the reference fluorescent sample as measured by the first instrument calibrated in the ultraviolet-included configuration;
obtaining a third measurement, the third measurement comprising the ratio of the sample channel raw signal to the reference channel raw signal for the reference fluorescent sample as measured by the first instrument operating in the ultraviolet-excluded configuration;
calculating the fluorescent spectral radiance factor of the reference fluorescent sample as measured by the first instrument, in accordance with the first measurement, the second measurement, and the third measurement.

15. A method for aligning measurements of fluorescent spectral radiance factors taken by a first instrument with measurements of fluorescent spectral radiance factors taken by a second instrument, the method comprising:
obtaining a first measurement, the first measurement comprising a total spectral radiance factor of a reference fluorescent sample as measured by the first instrument in an ultraviolet-included configuration;

obtaining a second measurement, the second measurement comprising the total spectral radiance factor of the reference fluorescent sample as measured by the second instrument in an ultraviolet-included configuration;

obtaining a third measurement, the third measurement comprising a reflectance of the reference fluorescent sample as measured by the first instrument in an ultraviolet-excluded configuration;

obtaining a fourth measurement, the fourth measurement comprising the reflectance of the reference fluorescent sample as measured by the second instrument in an ultraviolet-excluded configuration;

obtaining a fifth measurement, the fifth measurement comprising a total spectral radiance factor of a test fluorescent sample as measured by the first instrument in the ultraviolet-included configuration;

obtaining a sixth measurement, the sixth measurement comprising a reflectance of the test fluorescent sample as measured by the first instrument in the ultraviolet-excluded configuration; and estimating the fluorescent spectral radiance factor of the test fluorescent sample that would be measured by the second instrument, in accordance with the first measurement, the second measurement, the third measurement, the fourth measurement, the fifth measurement, and the sixth measurement, wherein the method is performed without knowledge of a matrix of a bispectral luminescent radiance factor of any sample.

16. The method of claim 15, wherein the first instrument and the second instrument are both configurable to operate in an ultraviolet-included mode and an ultraviolet-excluded mode.

17. The method of claim 16, wherein the first instrument and the second instrument are both calibrated prior to a performance of the method, using a white color standard, in both the ultraviolet-included mode and the ultraviolet-excluded mode.

18. A method for aligning measurements of fluorescent spectral radiance factors taken by a first instrument with measurements of fluorescent spectral radiance factors taken by a second instrument, the method comprising:

obtaining a first measurement, the first measurement comprising a ratio of a sample channel raw signal to a reference channel raw signal for a white color standard as measured by the second instrument calibrated in an ultraviolet-included configuration;

obtaining a second measurement, the second measurement comprising a ratio of a sample channel raw signal to a reference channel raw signal for a reference fluorescent sample as measured by the second instrument calibrated in the ultraviolet-included configuration;

obtaining a third measurement, the third measurement comprising the ratio of the sample channel raw signal to the reference channel raw signal for the reference fluorescent sample as measured by the second instrument operating in an ultraviolet-excluded configuration;

calculating a fluorescent spectral radiance factor of the reference fluorescent sample as measured by the second instrument, in accordance with the first measurement, the second measurement, and the third measurement;

obtaining a fourth measurement, the fourth measurement comprising the ratio of the sample channel raw signal to the reference channel raw signal for the white color standard as measured by the first instrument calibrated in an ultraviolet-included configuration;

obtaining a fifth measurement, the fifth measurement comprising the ratio of the sample channel raw signal to the reference channel raw signal for the reference fluorescent sample as measured by the first instrument calibrated in the ultraviolet-included configuration;

obtaining a sixth measurement, the sixth measurement comprising the ratio of the sample channel raw signal to the reference channel raw signal for the reference fluorescent sample as measured by the first instrument operating in an ultraviolet-excluded configuration;

calculating the fluorescent spectral radiance factor of the reference fluorescent sample as measured by the first instrument, in accordance with the fourth measurement, the fifth measurement, and the sixth measurement; and calculating an adjustment factor that aligns the measurements of fluorescent spectral radiance factors taken by the first instrument with the measurements of the fluorescent spectral radiance factors taken by the second instrument, in accordance with the fluorescent spectral radiance factor of the reference fluorescent sample as measured by the second instrument and the fluorescent spectral radiance factor of the reference fluorescent sample as measured by the first instrument.

19. The method of claim 18, wherein the first instrument and the second instrument are both configurable to operate in an ultraviolet-included mode and an ultraviolet-excluded mode.

20. The method of claim 19, wherein the first instrument and the second instrument are both calibrated prior to a performance of the method, using a white color standard, in the ultraviolet-included mode only.

* * * * *